United States Patent [19]

Yamaguchi et al.

[11] Patent Number: 4,475,553
[45] Date of Patent: Oct. 9, 1984

[54] ULTRASONIC NEEDLE HOUSING PROBE WITH CONTINUOUS LOCATOR ARRAY

[75] Inventors: Keiki Yamaguchi; Shinichi Sano; Hiromichi Akimoto; Takao Higashiizumi; Mineo Yamanaka; Takahiko Ishihara, all of Musashino, Japan

[73] Assignee: Yokogawa Hokushin Electric Corporation, Tokyo, Japan

[21] Appl. No.: 396,784

[22] Filed: Jul. 9, 1982

[51] Int. Cl.³ .............................................. A61B 10/00
[52] U.S. Cl. .................................................... 128/660
[58] Field of Search ............................... 128/660–663, 128/24 A

[56] References Cited

U.S. PATENT DOCUMENTS

| | | | |
|---|---|---|---|
| 4,108,165 | 8/1978 | Kopp et al. | 128/660 |
| 4,346,717 | 8/1982 | Haerten | 128/660 |
| 4,387,721 | 6/1983 | Enjoji | 128/660 |

Primary Examiner—Kyle L. Howell
Assistant Examiner—Francis J. Jaworski
Attorney, Agent, or Firm—Moonray Kojima

[57] ABSTRACT

An ultrasonic probe, such as for use in ultrasonography, comprising a support having a front end, which may be held against a human body, and a central groove in the side thereof for guiding a puncture needle to move therethrough, and an array of rectangular ultrasonic transducer elements mounted on and lying flatwise on the front end, wherein one or more ultrasonic transducer elements are located adjacent to an open end of the groove at the front end between the other transducer elements, whereby the image display of the needle is improved.

4 Claims, 2 Drawing Figures

ULTRASONIC NEEDLE HOUSING PROBE WITH CONTINUOUS LOCATOR ARRAY

BACKGROUND OF THE INVENTION

1. Field of Invention

This invention relates to an ultrasonic probe for use, for example, in taking biopsies, wherein a desired region of a human body is penetrated with a puncture needle while an organ to be examined is being monitored by ultrasonography.

2. Description of Prior Art

A conventional ultrasonic probe, for use with a puncture needle, has two separated arrays of ultrasonic transducers with a blank space therebetween which blank space is incapable of transmitting or receiving ultrasonic waves. The needle is guided through the blank space. Such a blank portion causes a vertical blank line to appear centrally on a sectional image displayed on a screed during a B-scan mode, thereby making the displayed image of the puncture needle, especially its pointed end, less clear on the screen. Thus, the prior art ultrasonic probes tended to produce inaccurate biopsies.

SUMMARY OF THE INVENTION

It is an object of the invention to provide an ultrasonic probe for use, with a puncture needle, in ultrasonography, wherein the probe is simple in construction and is capable of generating both an image of a vertical line serving as a guide for positioning accurately the puncture needle at a desired position on a body region, and a clear image of the pointed end of the needle.

According to the invention, an ultrasonic probe includes a support having on its front end, an array of ultrasonic transducer elements lying flatwise on the front end, and a groove in the support at the side thereof for guiding the needle. The groove forms an opening at the front end of the support, and one or more transducer elements are located adjacent the opening of the groove and between the other transducer elements, thus leaving no blank space on the front end of the support.

The foregoing and other objects, features and advantages of the invention will become more apparent from the following description and accompanying drawing.

DETAILED DESCRIPTION

Figure 1:
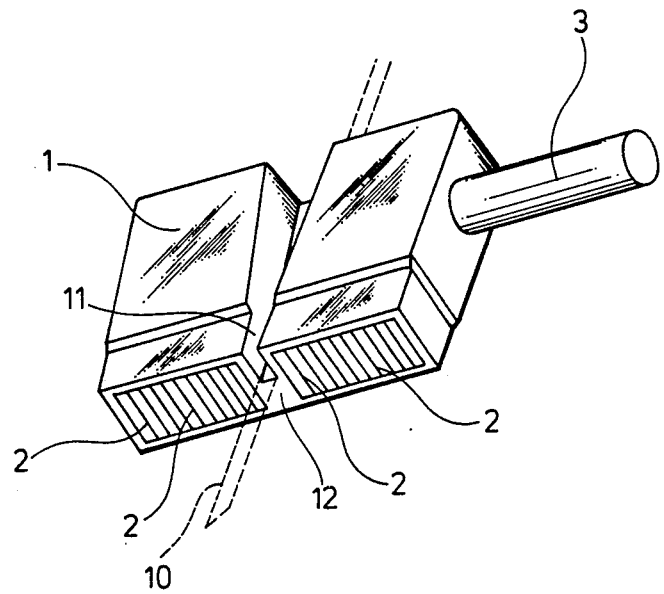
FIG. 1 is a perspective view depicting a prior art ultrasonic probe.

FIG. 1 illustrates a known ultrasonic probe comprising a support 1, and two separated arrays of ultrasonic transducer elements 2 for transmitting and receiving ultrasonic waves, as known in the art. The ultrasonic transducer elements 2 are each of rectangular shape and lie flatwise on and joined to a front end of the support 1, as depicted. The frontend may be held against a human body during examination, with the needle 10 being fed through groove 11, and operated by the elements 2 and support 1, as known in the art. The support 1 has a side portion thereof wherein a groove 11 is disposed, as shown. The central groove 11 is used for guiding a puncture needle 10 therethrough. The groove 11 opens at the front end, and diverges (i.e. progressively increases in width) away from the front end, such as in a V configuration as shown (see top perspective). Thus, groove 11 is defined by wall surfaces of the support extending substantially perpendicularly to the front end of support 1 for guiding puncture needle 10 to penetrate a desired region of the human body being examined, without the risk of being displaced out of an area in which ultrasonic energy is being radiated. Groove 11 is substantially V-shaped, when viewed from a side elevation view (or in the figure a top perspective) to permit puncture needle 10 to be smoothly advanced in a large range of puncture angles.

Ultrasonic probe 1 is electrically connected by a conductor wire 3 to an ultrasonographic diagnosing apparatus (not shown). Conductor wire is also electrically coupled with ultrasonic transducer elements 2, within support 1.

For effecting biopsies with the ultrasonic probe, the front end of support 1, on which ultrasonic transducer elements 2, are mounted, is brought into abutment against the surface of a test body, such as a human body. Then, the ultrasonic transducer elements 2 are linearly scanned to transmit and receive ultrasonic waves. While an organ to be examined is being thus monitored, puncture needle 10 is inserted through guide groove 11 into the test body.

The front end of support 1 has a central blank portion 12 by which the two arrays of ultrasonic transducer elements 2 are separated. Since blank portion 12 has no ultrasonic transducer elements thereon, it is incapable of transmitting and receiving ultrasonic waves. In a B-scan mode therefore, central blank portion 12 appears as a vertical blank line centrally on a sectional image displayed on a screen, with the result that the displayed image of the puncture needle, especially its pointed end, is rendered less clear on the display screen. Thus, inaccurate biopsies tend to result from use of prior art ultrasonic probes.

Figure 2:
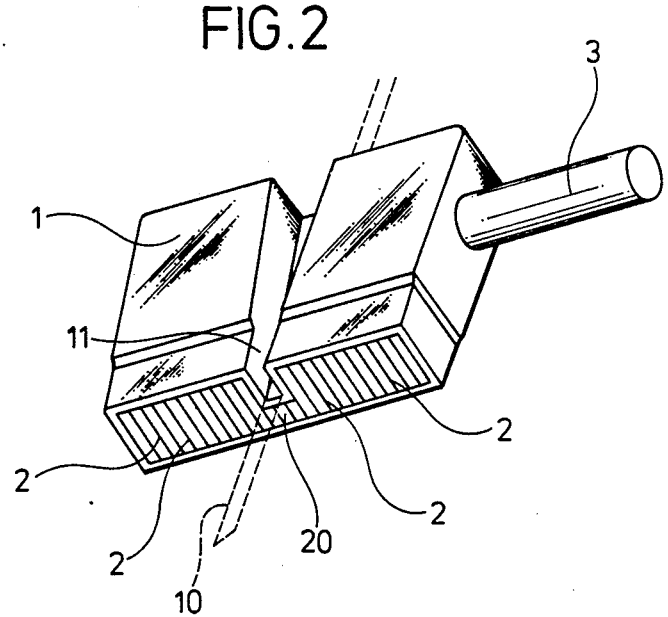
FIG. 2 is a perspective view depicting an illustrative embodiment of the invention.

The present invention is shown in FIG. 2, which differs from FIG. 1 in that one or more ultrasonic transducer elements 20 are located adjacent to the open end of the guide groove 11, and between the other transducer elements 2. The same components as shown in FIG. 1 are denoted with the same numerals for the sake of convenience and simplicity of description. The same functions of the embodiment of FIG. 2 are those of the probe shown in FIG. 1, except as herein described. The probe of the invention has transducer elements 20 which are shorter in width than the other elements 2. These elements 20 are similarly capable of transmitting and receiving ultrasonic waves. These elements, as shown, are positioned in successive relation to the elements 2, so that there is no blank space on the front end of support 1. The groove 11 for holding needle 10 diverges from the front end of support 1 in a V-shaped configuration, for example (see top perspective view) with the depth thereof being substantially constant. With the V shape, the needle 10 may be readily moved through a selected angle of positions.

When ultrasonic transducer elements 2 and 20 are linearly scanned, a central portion of a displayed sectional image is relatively dark and less clear as ultrasonic transducer elements 20 are of lower sensitivity than that of ultrasonic transducer elements 2. However, an echo image of the pointed end of needle 10, can be displayed more clearly than when a conventional probe is used to display needle 10. With the probe of this invention, the central vertical black line on a display screen can be lightened sufficiently, but still remain effective as a marking or guide for positioning needle 10 upon puncture. Such a lightened central vertical black line allows a portion of the sectional image to be displayed thereon.

Ultrasonic transducer elements 20 may be of the same or different depth, width or length, than the depth, width of length of the other ultrasonic transducer elements 2. However, the front end area about needle 10 should have transducers of sizes and shapes and dimensions, to perform the functions herein discussed. A receiver circuit (not shown) for ultrasonic transducer elements 20 may be adjusted in gain such that all of the ultrasonic transducer elements 2 and 20 will be of the same sensitivity for ultrasonic diagnosis. The gain of such a receiver circuit may also be changed dependent on whether puncture needle 10 is to be inserted or not.

The number of elements 2 and 20 may vary according to need. For purposes of the invention, the element or elements 20 should continuously connect elements 2 so that on the end surface the needle 10 will be enclosed on three sides with the transducer elements.

With the ultrasonic probe constructed according to the invention, one or more less sensitive ultrasonic transducer elements (e.g. 20) are located adjacent to the central needle groove 11 and between the other transducer elements (e.g. 2), so that an array of uninterrupted ultrasonic transducer elements are mounted on the front of support 1. This arrangement allows the pointed end of needle 10 to be displayed as a clearer echo image than when the prior ultrasonic probe is used. A central vertical line remains on a displayed image with sufficient darkness to serve as a visual guide for positioning the puncture needle, and yet not obscure the image on the vertical line. Accordingly, the ultrasonic probe of the invention is of great practical value and advantage, and can be used to effect more accurate biopsies.

The foregoing description is illustrative of the principles of the invention. Numerous other modifications and extensions thereof would be apparent to the worker skilled in the art. All such modifications and extensions are to be considered to be within the spirit and scope of the invention.

What is claimed is:

1. An ultrasonic probe, for use with a needle in ultrasonography, comprising
    a support structure having a first end of substantially rectangular shape and substantially flat surface, a second end, and at least a first side and a second side extending between said first and second ends, said first side having a groove defined therein and extending from at least said first end and to said second end and being open at said first end, said groove serving to guide said needle; and
    a plurality of elongated ultrasonic transducer elements disposed on said surface of said first end outside of said open end of said groove in said first end and substantially parallel to each other and extending substantially from said first side to said second side of said first end; wherein a number of said plurality of said elements extend from said groove opening
    to said second side, and wherein said first side is opposite said second side.

2. The probe of claim 1, wherein said groove has two flat oppositely disposed sides which diverge in a substantially V-shaped configuration, away from said first end, and wherein said groove also has a substantially constant depth extending into said first end.

3. An ultrasonic probe, for use with a needle in ultrasonography, comprising a support structure having a first end of substantially rectangular shape and substantially flat surface, a second end, and a plurality of sides extending between said first and second ends, one of said sides having a groove defined therein and extending from at least said first end to said second end and being open at said first end, said groove serving to guide said needle; and
    a plurality of elongated ultrasonic transducer elements disposed on said surface of said first end outside of said open end of said groove in said first end and substantially parallel to each other and extending substantially from one side to another side of said first end; wherein a number of said plurality of said elements being disposed surrounding said groove opening in said first end;
    wherein said elements are substantially equal in width, and wherein a part of said plurality of said elements extend substantially from said one side to said other side and are substantially equal in elongated length; and wherein a remainder of said plurality of elements extend substantially from said groove opening to said other side, and are of a shorter elongated length than said length of said part of said plurality of elements, and wherein said one side is disposed opposite said other side.

4. The probe of claim 3, wherein said groove has two flat oppositely disposed sides which diverge in a substantially V-shaped configuration, away from said first end, and wherein said groove also has a substantially constant depth extending into said first end.

* * * * *